United States Patent
Uchikubo et al.

(10) Patent No.: US 6,490,490 B1
(45) Date of Patent: Dec. 3, 2002

(54) REMOTE OPERATION SUPPORT SYSTEM AND METHOD

(75) Inventors: Akinobu Uchikubo, Oume (JP); Hitoshi Mizuno, Koganei (JP); Masakazu Gotanda, Kanagawa (JP)

(73) Assignee: Olympus Optical Co., Ltd. (JP)

( * ) Notice: Subject to any disclaimer, the term of this patent is extended or adjusted under 35 U.S.C. 154(b) by 0 days.

(21) Appl. No.: 09/523,355

(22) Filed: Mar. 10, 2000

Related U.S. Application Data

(63) Continuation-in-part of application No. 09/434,728, filed on Nov. 5, 1999, now abandoned.

(30) Foreign Application Priority Data

| Nov. 9, 1998 | (JP) | ............................................ 10-318019 |
| Mar. 19, 1999 | (JP) | ............................................ 11-076334 |
| Mar. 19, 1999 | (JP) | ............................................ 11-076335 |

(51) Int. Cl.$^7$ ............................................ G05B 19/18
(52) U.S. Cl. ............................. 700/65; 700/17; 700/66; 700/83; 700/246; 700/250; 600/101; 600/104; 600/112; 600/118; 600/160
(58) Field of Search ............................. 700/17, 64, 65, 700/66, 83–88, 246, 250; 600/101–104, 109–111, 112, 114, 117–118, 126, 166–167, 160, 173, 407; 604/246; 606/157; 704/258

(56) References Cited

U.S. PATENT DOCUMENTS

| 5,313,306 | A | * | 5/1994 | Kuban et al. ................ 348/240 |
| 5,589,874 | A | * | 12/1996 | Buchin ........................ 348/588 |
| 5,928,137 | A | * | 7/1999 | Green ........................... 600/104 |
| 6,016,439 | A | * | 1/2000 | Acker .......................... 600/411 |
| 6,178,346 | B1 | * | 1/2001 | Amundson et al. ............ 348/77 |
| 6,221,007 | B1 | * | 4/2001 | Green ........................... 600/104 |
| 6,241,657 | B1 | * | 6/2001 | Chen et al. ................... 600/117 |
| 6,249,713 | B1 | * | 6/2001 | Geiger et al. .................. 378/42 |
| 6,346,940 | B1 | * | 2/2002 | Fukunaga .................... 345/420 |

FOREIGN PATENT DOCUMENTS

| JP | 9-149879 | 6/1997 |

* cited by examiner

*Primary Examiner*—Ramesh Patel
(74) *Attorney, Agent, or Firm*—Ostrolenk, Faber, Gerb & Soffen, LLP

(57) ABSTRACT

According to a remote operation support system, a physician present in a remote place can view endoscopic images displayed in an operating room over a communication line, and change an image area or a viewing direction represented by endoscopic images in a desired manner by performing manipulations. The physician present in the remote place can thus support an operator present in the operating room. An endoscope system installed in the operating room and a remote control system installed in a control room located in the remote place are linked using a public communication line. The endoscope system has a signal transmission apparatus installed in the operating room. The signal transmission apparatus in the operating room converts a video signal and a control signal or patient data, which are produced by a CCU and a system controller respectively, and outputs resultant signals over the public line. The remote control system has a signal transmission apparatus installed in the control room. The signal transmission apparatus in the control room is connected on the public line and converts the transmitted signals into the original signals. A second monitor and a remote controller are connected to the transmission apparatus.

12 Claims, 9 Drawing Sheets

REMOTE OPERATION SUPPORT SYSTEM AND METHOD

This application is a CIP of Ser. No. 09/434,728, filed Nov. 15, 1999, now abandoned.

BACKGROUND OF THE INVENTION

1. Field of the Invention

The present invention relates to a remote operation support system and method permitting an operator in an operating room to perform an operation with the help of instructions given by a supporter present in a remote place.

2. Description of the Related Art

Endoscopes are today widely adopted in the fields of medicine and industries. Endoscope systems in which endoscopic images produced by an endoscope with an external TV camera or an electronic endoscope are displayed on a monitor and viewed for observing or treating a lesion have been widely used in recent years. The endoscope with an external TV camera has a TV camera with a built-in imaging means mounted on an eyepiece unit of an optical endoscope. The electronic endoscope has an imaging means incorporated in the distal part thereof.

As one of the endoscope systems, an endoscope system making it possible to perform a treatment or an operation under endoscopic observation using, in addition to a light source apparatus, a camera control unit, and a TV monitor, a plurality of peripheral instruments, for example, a pneumoperitoneum unit and a high-frequency cautery has been constructed and put to practical use. The light source apparatus supplies illumination light to an endoscope. The camera control unit (also referred to as a video processor) has an image signal processing circuit that enables display of endoscopic images. Endoscopic images are displayed on the TV monitor.

In the above endoscope system, the plurality of peripheral instruments is normally connected to a system controller and controlled on a centralized basis.

In the case of trans-endoscopic surgery, even a physician having little experience can achieve surgery with the help of instructions given by an well-experienced physician who views endoscopic images displayed on the monitor. Therefore, the endoscopic images displayed on the monitor are very important. If the endoscopic images should represent an area different from an operative area desired by the well-experienced physician, the well-experienced physician would give oral or direct instructions. Thus, the physician teams up with the well-experienced physician so as to achieve surgery smoothly.

The well-experienced physician giving instructions may be present in, for example, a remote place. In this case, a hospital or the like in the remote place for which a physician serving as a supporter works and an operating room in which a physician in charge of a surgical procedure are linked using a public line. This results in a system for supporting the physician in the operating room so that the physician can properly perform an operation on a patient while receiving instructions from the physician present in the remote plate.

By the way, in the trans-endoscopic surgery in which an endoscope is used during surgery, endoscopic images displayed on a view screen of a monitor and representing an operative area are very important. If the endoscopic images should represent an area other than a desired region, an examination or treatment cannot be achieved properly.

For example, Japanese Unexamined Patent Publication No. 9-149879 has proposed an endoscope system capable of visualizing a treatment instrument such as forceps and its surroundings using a view screen and preventing the view screen from becoming hard to see. The conventional endoscope system includes an XY stage control unit for giving control so that a reference circle will be positioned in a field of view offered by an endoscopic and magnified by a magnification optical system. The reference circle has a radius r and has a center thereof aligned with the center P of a rectangular TM area within an image range whose image is magnified by the magnification optical system and displayed on a TV monitor. As another related art, an endoscope system making it possible to move or change a field of view using a switch included in an endoscope has been proposed.

However, in the endoscope system described in the Japanese Unexamined Patent Publication No. 9-149879 or the endoscope system having the endoscope whose field of view can be moved, if the field of view is moved to a desired position at a too high speed, the field of view may pass through the desired position. In these conventional endoscope systems, a manipulation-related instruction must be repeatedly entered in order to move the field of view to a desired position. It therefore takes much time to move the field of view to a desired position.

In contrast, the field of view may be moved at a lower speed so that the field of view can be moved to a desired position with the first move. The field of view can be moved to the desired position reliably. However, since the moving speed is low, it takes much time. to move the field of view to the desired position. While manipulations are performed in order to move the field of view, a treatment using a treatment instrument cannot be carried out. This becomes a factor in retarding the progress of surgery.

SUMMARY OF THE INVENTION

An object of the present invention is to provide a remote operation support system and method permitting a physician in a remote place to properly support a physician in an operating room. Specifically, the physician in the remote place can view endoscopic images by way of a communication line. Besides, the physician in the remote place can change an image area or a viewing direction, which is represented by endoscopic images displayed on a monitor, in a desired manner by performing manipulations.

Another object of the present invention is to provide a remote operation support system and method making it possible to move a field of view to a desired position quickly, easily, and reliably.

According to the present invention, there is provided a remote operation support system in which an operating room and a control room located away from the operating room are linked using a communication line so that an operator in the operating room can perform an operation while being supported by a supporter in the control room.

An endoscopic imaging system, an image processing unit, a first display unit, a field-of-view change control unit, and a first signal transmission apparatus are installed in the operating room. The endoscopic imaging system includes an image formation optical system and an imaging device. The image processing unit converts an image signal produced by the endoscopic imaging system into a video signal. The first display unit displays endoscopic images expressed by the video signal sent from the image processing unit. The field-of-view change control unit changes an image area or a viewing direction offered by the endoscopic imaging system. The first signal transmission apparatus transmits a signal processed by the image processing unit over the communication line or receives an input signal over the communication line.

A second signal transmission apparatus, a second display unit, a control unit, and an input unit are installed in the control room. The second signal transmission apparatus receives a signal from the first signal transmission apparatus over the communication line or transmits a signal from the control room. The second display unit displays images according to an endoscopic video signal received by the second signal transmission apparatus. The control unit produces an instruction signal used to change the image area or viewing direction represented by endoscopic images displayed on the second display unit. The control unit also controls the field-of-view change control unit in the operating room by way of the second signal transmission apparatus and transmission line.

According to the present invention, there is provided a remote operation support method in which an operating room and a control room located away from the operating room are linked using a communication line so that an operator in the operating room can perform an operation while being supported by a supporter in the control room.

The remote operation support method consists mainly of an imaging step, a converting step, a video signal transmitting step, a video signal receiving step, a displaying step, an outputting step, an instruction signal transmitting step, an instruction signal receiving step, and a changing step. At the imaging step, an intracavitary region of an object lying in the operating room is imaged. At the converting step, a signal expressing endoscopic images projected at the imaging step is processed and converted into a video signal. At the video signal transmitting step, the video signal is transmitted to the control room. At the video signal receiving step, the video signal transmitted from the operating room is received. At the displaying step, endoscopic images are displayed according to the received video signal. At the outputting step, an instruction signal is produced and output for use in changing an image area or a viewing direction represented by the endoscopic images displayed at the displaying step. At the instruction signal transmitting step, the instruction signal produced and output at the outputting step is transmitted to the operating room. At the instruction signal receiving step, the instruction signal transmitted at the instruction signal transmitting step is received in the operating room. At the changing step, the image area or viewing direction in an intracavitary region of an object is changed based on the received instruction signal.

Other features of the present invention and advantages thereof will be fully apparent from the description below.

BRIEF DESCRIPTION OF THE DRAWINGS

FIG. 1 is an explanatory diagram for explaining a schematic configuration employed in a method of controlling the field of view of an endoscopic camera;

FIG. 2 is an explanatory diagram for explaining the configuration of a second controller for use in remotely giving support;

FIG. 3 is an explanatory diagram for explaining a display screen of a display device;

FIG. 4 is a graph clarifying the relationship between a moving speed at which a field of view represented by endoscopic images is moved and a destination;

FIG. 6 shows the configuration of a remote operation support system;

FIG. 7 shows the configuration of a signal converter shown in FIG. 6;

FIG. 8 shows the configuration of a system controller shown in FIG. 6;

DESCRIPTION OF THE PREFERRED EMBODIMENTS

Embodiments of the present invention will be described with reference to the drawings below.

Figure 1:
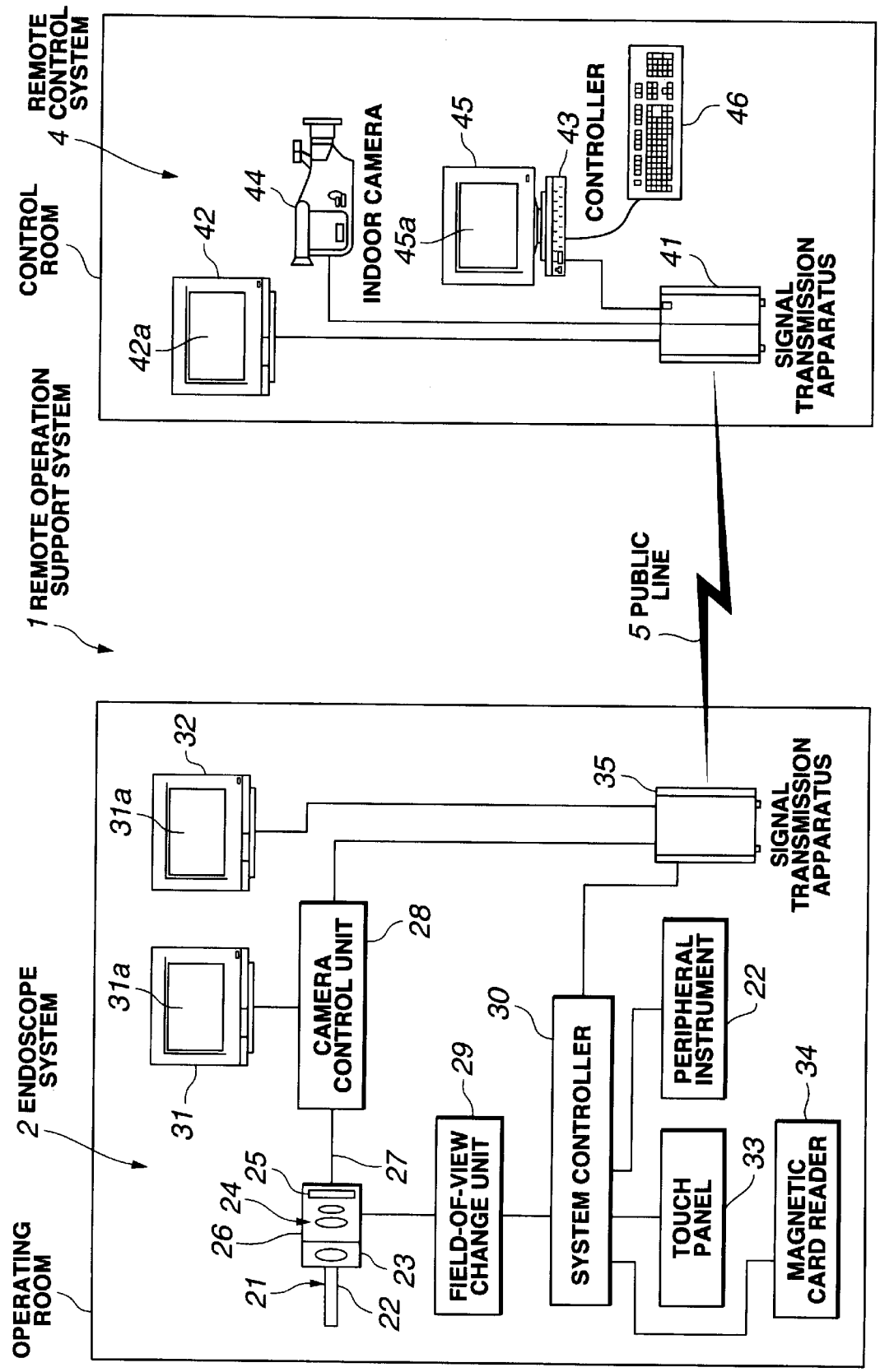
FIG. 1 to FIG. 4 relate to the first embodiment of the present invention.
Figure 2:
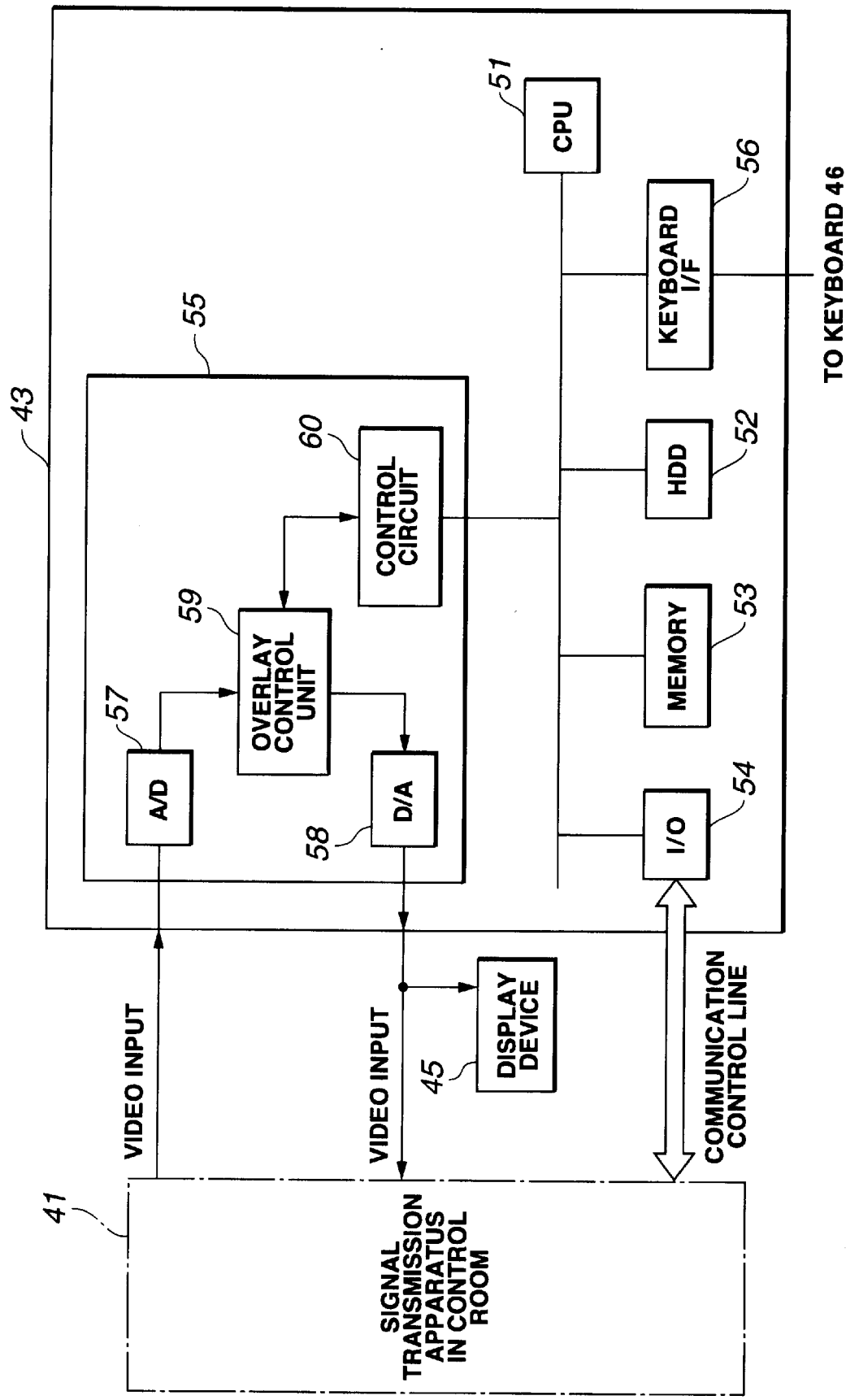
Figure 3:
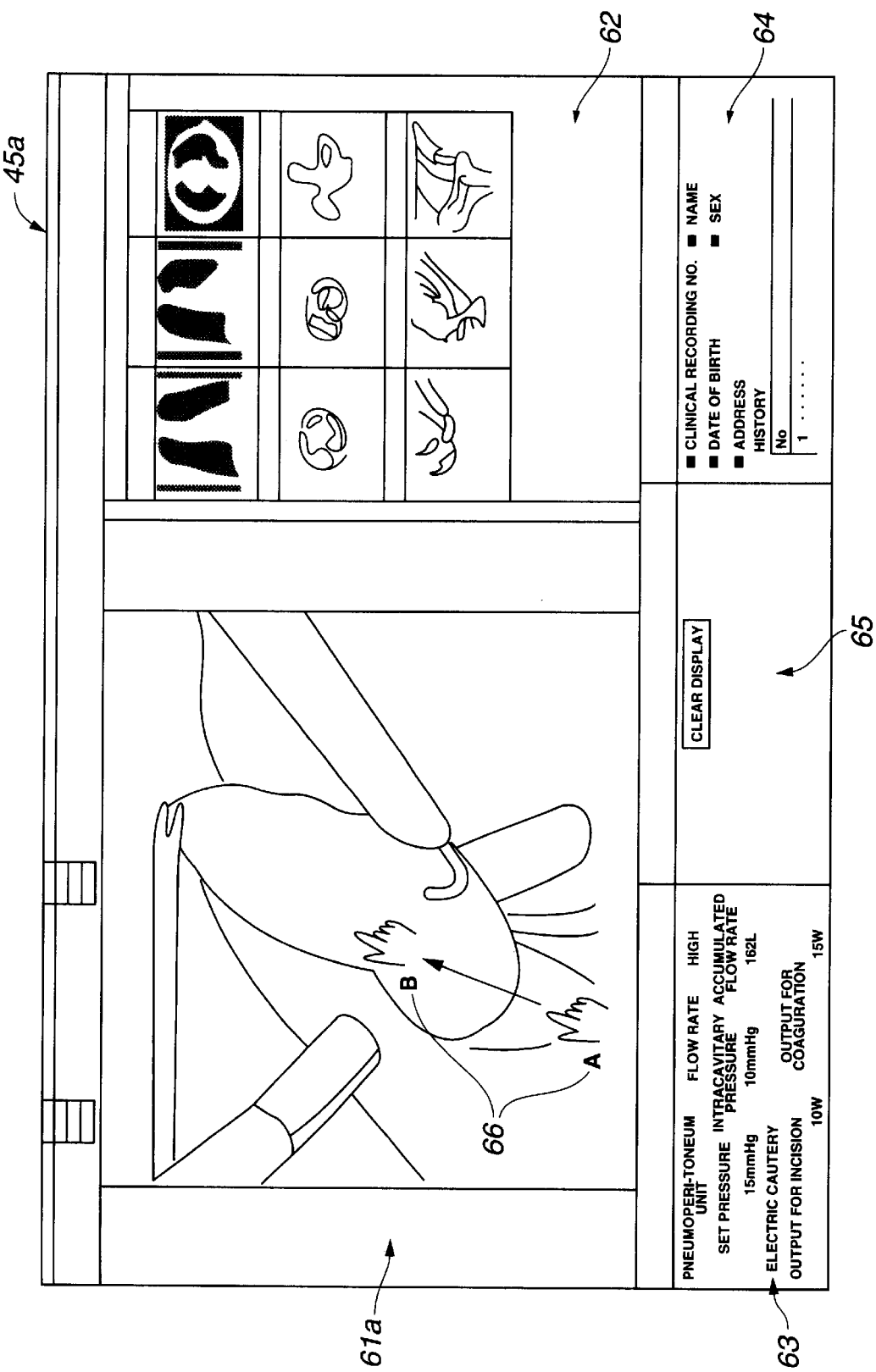
Figure 4:
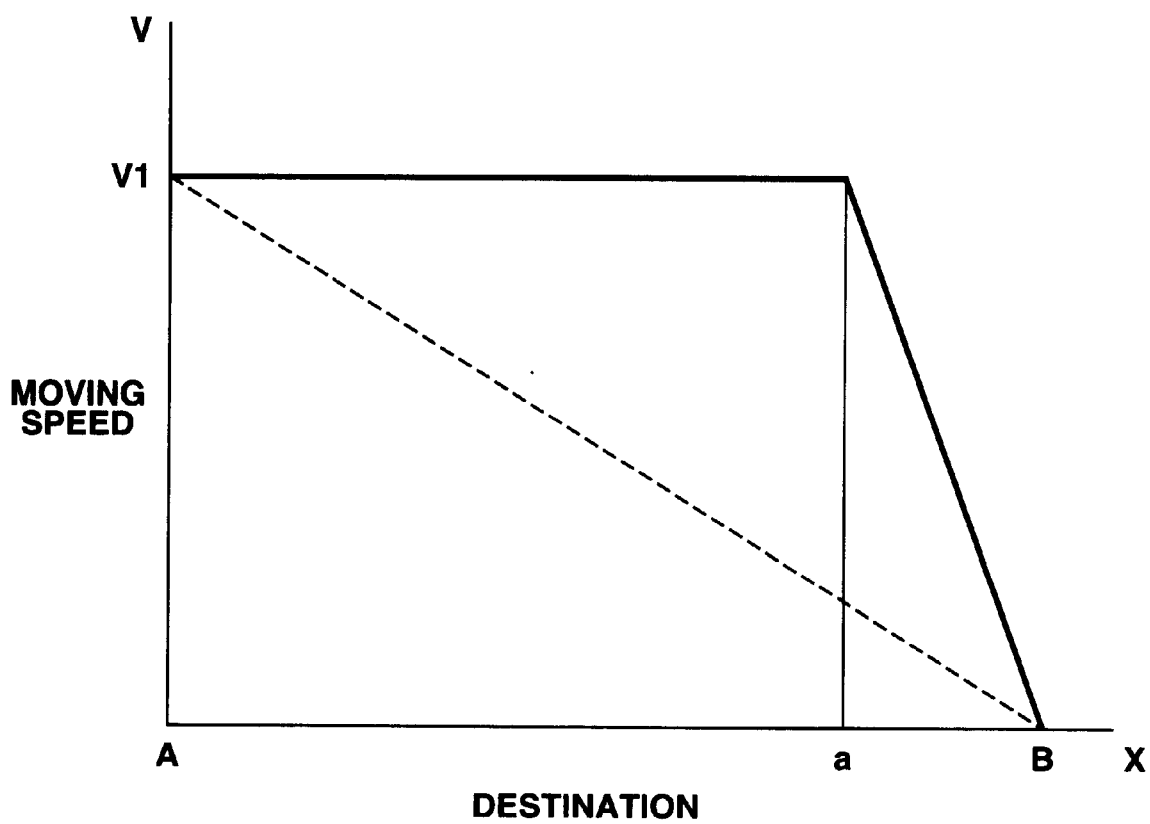

FIG. 1 to FIG. 3 relate to the first embodiment of the present invention. FIG. 1 shows the schematic configuration of a remote operation support system. FIG. 2 is an explanatory diagram for explaining the configuration of a second controller for use in remotely giving support. FIG. 3 is an explanatory diagram for explaining a display screen of a display device. FIG. 4 is a graph clarifying the relationship between a moving speed, at which a field of view represented by endoscopic images is moved, and a destination.

According to the first embodiment, there is provided a remote operation support system in which an operating room and a control room located in a remote place are linked using a communication line so that an operator in the operating room can perform an operation with the help of instructions and advises given from a supporter such as a physician present in a control room.

As shown in FIG. 1, a remote operation support system 1 in accordance with the present invention has an endoscope system 2 and a remote control system 4 linked using a public line 5 that is a communication network, such as, an integrated services digital network (ISDN). The endoscope system 2 is installed in an operating room, while the remote control system 4 is installed in a control room located in, for example, a remote place away from the endoscope system 2. The H.320 and other standards have been enacted to stipulate rules according to which images, voice, and data are transmitted over the public line. Therefore, images, voice, and data will be transmitted over the ISDN in conformity with the H320 and other standards.

The endoscope system 2 installed in the operating room consists mainly of an endoscope 21 for use in observing an intracavitary region of a patient, and a peripheral instrument 22 such as an electric cautery, a pneumoperitoneum unit, or an ultrasonic surgical instrument used to perform a treatment or cure. Driving power is supplied to the peripheral instrument 22 over, for example, a cord. The output value of driving power can be varied.

The endoscope 21 is of a type having, for example, a rigid insertion unit 21a. A TV camera 26 serving as an endoscopic imaging means is mounted on an eyepiece unit 23 formed at the rear end of the insertion unit 21a so that the TV camera 26 can be dismounted freely. The TV camera 26 has an image formation optical system 24 composed of a plurality of optical lenses and a charge coupled device (CCD) 25 serving as an imaging device incorporated therein.

A light guide cable that is not shown is extended from the endoscope 21 and coupled to a light source apparatus that is not shown. Illumination light emanating from a lamp incorporated in the light source apparatus is propagated to the distal end of the insertion unit 21a over the light guide cable and a light guide lying through the endoscope 21. The illumination light is radiated through an illumination window that is not shown, thus illuminating an intracavitary region.

An objective lens that is not shown is locked in an observation window adjoining the illumination window. An optical image of an object is formed on a distal lens belonging to a system of relay lenses, which serves as an optical image propagating means, incorporated in the insertion unit 21a. The optical image is then relayed to a rearmost lens belonging to the system of relay lenses, and seen magnified through the eyepiece unit 23.

The optical image propagated through the system of relay lenses is formed on the CCD 25 included in the TV camera 26 mounted on the eyepiece unit 23. An image signal photoelectrically converted by the CCD 25 is transmitted to a camera control unit (CCU) 28 serving as an image processing means over a signal cable 27. The CCU 28 produces a standard video signal.

The video signal produced by the CCU 28 is output to a first monitor 31 serving as a first display means, and endoscopic images taken by the endoscope 21 are displayed on a monitor screen 31a.

A field-of-view change unit 29 serving as a field-of-view control means is connected to the TV camera 26. The field-of-view change unit 29 moves at least one of the image formation optical system 24 and CCD 25 so as to change an image area or a viewing direction.

The field-of-view change unit 29, CCU 28, and peripheral instrument 22 are connected to a system controller 30 serving as a first control means and controlling them. A touch panel 33 for use in entering an instruction and a magnetic card reader 34 for inputting patient data or the like are connected to the system controller 30.

When an instruction is entered using, for example, the touch panel 33, a tone controlled by the CCU 28, a distance between the image formation optical system 24 and CCD 25, and power to be output to the peripheral instrument 22 is be changed by the system controller 30. More particularly, when the peripheral instrument 22 is, for example, an electric cautery, the output level of electric energy supplied for incision or coagulation can be set using the touch panel or the like. When the peripheral instrument 22 is a pneumoperitoneum unit, a set pressure can be changed using the touch panel or the like.

The magnetic card reader 34 reads patient data from a magnetic card, and inputs the patient data to the system controller 30. The patient data is then output from the system controller 30 to the CCU 28. Consequently, the patient data can be superimposed on endoscopic images.

The CCU 28 and system controller 30 are connected to the signal transmission apparatus 35, which serves as a first signal transmitting means, in the operating room. The signal transmission apparatus 35 in the operating room converts a video signal, which expresses endoscopic images and is produced by the CCU 28, and a control signal or patient data controlled by the system controller 30 into signals transmissible over the public line 5. The resultant signals are then output to the control room over the public line 5 on which the signal transmission apparatus 35 in the operating room is connected.

The signal transmission apparatus 35 in the operating room converts signals, which are converted by a signal transmission apparatus 41 in the control room that will be described later, and input over the public line 5, into an original video signal and an original instruction signal. The instruction signal is output to the system controller 30, while the video signal is output to an auxiliary monitor 32 connected to the signal transmission apparatus 35 in the operating room. Image information sent from the control room is displayed on the monitor screen 32a.

A keyboard that is not shown is connected as an input means to the system controller 30. A comment or the like can be transmitted from the keyboard to a supporter in the control room by way of the system controller 30, the signal transmission apparatus 35 in the operating room, and the public line 5.

The remote control system 4 installed in the control room consists mainly of the signal transmission apparatus 41, a second monitor 42, a remote controller 43, and an indoor camera 44. The signal transmission apparatus 41 in the control room is connected on the public line 5. The signal transmission apparatus 41 converts signals, which are input from the signal transmission apparatus 35 in the operating room over the public line 5, into a video signal produced by the CCU 28 and a control signal or patient data controlled by the system controller 30. The second monitor 42 is connected to the signal transmission apparatus 41 in the control room, and is one of monitors for displaying endoscopic images according to the video signal output from the signal transmission apparatus 41 in the control room. The remote controller 43 is connected to the signal transmission apparatus 41 in the control room, and serves as a second control means. The control signal or patient data output from the signal transmission apparatus 41 in the control room is input to the remote controller 43. A program for calculating a distance by which a field of view is moved is installed in the remote controller 43. The indoor camera 44 is connected to the signal transmission apparatus 41 in the remote room, and used to image a drawing or table present in the control room or the supporter's expression.

A display device 45 serving as a second display means is connected to the remote controller 43. The display device 45 captures endoscopic images sent from the CCU 28 as still images, and superimposes patient information or the like sent from the system controller 30 on the endoscopic images. An input means for use in entering the contents of control, for example, a touch panel or a keyboard 46 is connected to the remote controller 43. A pointing device such as a mouse that is not shown is also connected as an input means.

As shown in FIG. 2, the remote controller 43 consists mainly of a central processing unit (CPU) 51, a hard disk drive (HDD) 52, a memory 53, an input/output (I/O) interface 54, a video capture control unit 55, and a keyboard interface 56. The CPU 51 is responsible for control. operation programs each directing the cPu 51 to carry out a take and images are saved in the hard disk drive 52. The memory 53 is used to temporarily store images or used as a work area. The I/O interface 54 facilitates input or output of data to or from the signal transmission apparatus 41 in the control room. The video capture control unit 55 captures a video signal and superimposes data on images. The keyboard interface 56 is connected to, for example, the keyboard 46. The CPU 51, hard disk drive 52, memory 53, I/O interface 54, video capture control unit 55, and keyboard interface 56 are interconnected over a bus.

Communication of a control signal to the signal transmission apparatus 41 in the control room is achieved through the I/O interface 54. The operation programs each directing the remote controller 43 to carry out a task are saved in the HDD 52.

Assume that setting is carried out using the touch panel 33 in the operating room in order to cause the system controller 30 to control the action of the peripheral instrument 22. The contents of control are stored in the memory 53 through the I/O interface 54 in the remote controller 43 by way of the signal transmission apparatus 35 in the operating room, the public line 5, and the signal transmission apparatus 41 in the control room.

Moreover, patient information input from the magnetic card reader 34 to the system controller 30 is also stored in the memory 53 through the I/O interface 54 in the remote controller 43.

The video capture control unit 55 is connected to the signal transmission apparatus 41 in the control room. The video capture control unit 55 has an A/D converter 57 for digitizing an input video signal and a D/A converter 58 for converting the video signal into an analog form and outputting a resultant signal.

The A/D converter 57 and D/A converter 58 are connected to an overlay control unit 59 for controlling an overlay. The overlay control unit 59 is connected to a control circuit 60 for controlling the overlay control unit 59 and transferring data. The control circuit 60 is connected on the bus.

According to the present embodiment, communication of images from the signal transmission apparatus 41 in the control room is achieved via the A/D converter 57 and D/A converter 58 included in the video capture control unit 55.

A video signal input through the A/D converter 57 is converted into an image signal by the overlay control unit 59 under the control of the control circuit 60. An output of the overlay control unit 59 is transferred to the signal transmission apparatus 41 in the control room via the D/A converter 58. Communication of the signal transmission apparatus 41 in the control. room with the remote controller 43 is controlled by the CPU 51 according to a program saved in the HDD 52.

An image captured by the video capture control unit 55 can be saved in the HDD 52. When keys of the keyboard 46 are pressed in order to enter an instruction to select an image, the CPU 51 receives the instruction to select an image, and outputs thumbnail images of the selected image to the video capture control unit 55. The overlay control unit 59 superimposes the thumbnail image signals on the video signal (sent from the signal transmission apparatus 35 in the operating room).

The video signal transferred from the D/A converter 58 is also output to the display device 45. Images shown in FIG. 3 are displayed on the display device 45.

As shown in FIG. 3, a display area 45a on the display device 45 is divided into a screen display area 61, a thumbnail display area 62, a state-of-peripheral instrument display area 63, a patient information display area 64, and a comment display area 65.

Endoscopic images sent from the CCU 28 and a thumbnail image selected from the thumbnail display area 62 are displayed in the screen display area 61. Images produced by reducing in size reference images, or images (thumbnail images) produced by reducing in size still images are displayed in the thumbnail display area 62. The reference images are expressed by image data stored in the remote controller 43. The still images are expressed by the video signal and correspond to the endoscopic images sent from the CCU 28. The controlled states of the peripheral instrument 22 and CCU 28 sent from the system controller 30 are displayed in the state-of-peripheral instrument display area 63. Patient information sent from the system controller 30 is displayed in the patient information display area 64. A comment sent from the operating room is displayed in the comment display area 65. The comment is entered at the keyboard or the like, remarking what the operator in the operating room has noticed during a surgical procedure. Consequently, the supporter in the control room can provide support information while viewing the endoscopic images displayed on the second monitor 42 and display device 45.

The input means such as the keyboard 46 or mouse is used to enter support information such as an instruction or notice concerning surgery. The support information is then superimposed on the images appearing in the screen display area 61 of the display area 45a. The support information is then displayed in the screen 32a of the auxiliary monitor 32 in the operating room by way of the signal transmission apparatuses 41 and 35 and the public line 5. Consequently, the operator in the operating room can proceed with a surgical procedure with the help of the support information sent from the control room in a remote place and displayed on the auxiliary monitor 32.

The program for calculating a distance by which a field of view is moved is saved in the HDD 52. Position information entered using the input means such as the keyboard 46 or a mouse is stored in the memory 53 via the keyboard interface 56 or I/O interface 54.

Assume that point A pointed out with a cursor 66 appearing in the screen display area 61 shown in FIG. 3 is clicked and dragged to point B while kept clicked. Position information of points A and B are then stored in the memory 53 in the remote controller 43. The program saved in the HDD 52 calculates a destination using at least one of a distance by which a field of view is moved, that is, a magnitude of shift from point A to point B, a moving direction that is an angle of shift, and a moving speed that is a speed of shift. The distance by which the point is moved, the moving direction, and the moving speed are derived from the position information. Consequently, an instruction signal to be output to the field-of-view change unit 29 is produced.

The instruction signal stemming from the calculation is output to the system controller 30 by way of the signal transmission apparatuses 41 and 35 and the public line 5. In response to the instruction signal, the system controller 30 changes the distance between the image formation optical system 24 and CCD 25 using the field-of-view change unit 29 according to the results of the calculation. Consequently, endoscopic images representing a field of view or an image area are displayed in the screen display area 61 in such a manner that a point in the field of view corresponding to point A appears at point B in the screen display area 61.

Referring to FIG. 4, the relationship between a moving speed at which an image area or field of view represented by endoscopic images is moved and a destination will be described below.

The axis of abscissas in the graph indicates a distance by which a field of view is moved, and the axis of ordinates indicates a moving speed.

In FIG. 4, a first line that is a solid line indicates the relationship between a destination to which the field of view is moved until it reaches point B in an area of interest from point A through point a, and a speed at which the field of view is moved. The field of view is moved at a high moving speed V1 from point A to point a, and then moved with the moving speed reduced from point a to point B.

In other words, the field of view is moved to a destination, which is away from the area of interest, at a high speed. The moving speed is reduced as the field of view approaches point B. Consequently, the field of view is moved quickly to near the area of interest. When the field of view approaches point B in the area of interest, the moving speed is low enough to make endoscopic images easy to see.

A second line that is a dashed line in the graph indicates that a moving speed at which the field of view is moved from point A to point B is reduced linearly in relation to the distance to point B. Consequently, the field of view is moved quickly to the area of interest. When the field of view approaches point B in the area of interest, the moving speed is low enough to make endoscopic images easy to see.

According to the present embodiment, after point B is designated as a predetermined position, a field of view is moved to point B. Alternatively, the predetermined position may not be designated every time but may be fixed to, for example, a center of a screen or any predetermined position. The field of view may then be moved to the predetermined position.

To be more specific, the supporter views the endoscopic images displayed on the monitor screen 42a of the second monitor 42. When the supporter notices that the displayed endoscopic images do not represent a desired image area or a desired viewing direction, the supporter overlays the screen display area 61 of the display device 45 with an endoscopic image currently displayed on the second monitor 42. Thereafter, the input means such as the keyboard 46 or mouse is used to give an instruction to change the image area or viewing direction using the field-of-view change unit 29.

The instruction information entered using the input means is transmitted in the form of an instruction signal from the remote controller 43 to the system controller 30 in the operating room by way of the signal transmission apparatuses 41 and 35 and the public line 5. The system controller 30 outputs a control signal, which instructs change of the distance between the image formation optical system 24 and CCD 25, to the field-of-view change unit 29 according to the instruction information. In response to the control signal, the field-of-view change unit 29 changes the distance between the image formation optical system 24 and CCD 25 by moving at least one of the image formation optical system 24 and CCD 25.

Consequently, desired endoscopic images designated by the supporter in the control room are displayed in the monitor screens 31a and 42a of the first monitor 31 and second monitor 42 and in the display area 45a of the display device 45.

For changing the tone of endoscopic images appearing in the monitor screens 31a and 42a and the display area 45a, the input means such as the keyboard 46 or a mouse is used to change the controlled state of the CCU 28 which is displayed in the state-of-peripheral instrument display area 63. An instruction signal is then produced, and transmitted to the system controller 30 in the operating room by way of the signal transmission apparatuses 41 and 35 and the public line 5. In response to the instruction signal, the system controller 30 sends a control signal to the CCU 28 so as to change the tone.

According to the present embodiment, the supporter in a remote place can view endoscopic images representing a region, which undergoes surgery in the operating room, using the second monitor and display device, and can acquire patient information.

According to the system, the input means is used to manipulate endoscopic images appearing on the display device, and the field-of-view change unit in the operating room is directly controlled over a communication line. Thus, desired endoscopic images can be displayed in the monitor screen. According to the present system, the supporter in a remote place uses a touch panel or a mouse to designate a desired point in an endoscopic image currently displayed on the display device. Consequently, desired endoscopic images representing a field of view-containing the designated point can be displayed.

According to the present system, when a field of view represented by endoscopic images is moved, it is moved at a high speed from an original to an area of interest. The moving speed is reduced as the field of view approaches an intended point in the area of interest. Otherwise, as the field of view moves from the original to the intended point, the moving speed may be reduced linearly in relation to the distance to the intended point. Consequently, the field of view can be moved quickly. Besides, as the field of view approaches the intended point in the area of interest, the moving speed is low enough to make endoscopic images easy to see.

According to the present system, a surgical procedure can be grasped nearly in real time in the remote place, and support information helpful in carrying out the surgical procedure properly can be supplied from the remote place to the operator in the operating room. Moreover, however microscopic the surgical procedure is, the surgical procedure can be grasped accurately and quickly, and supported smoothly and timely.

According to the present embodiment, the public line 5 is used as the communication line linking the signal transmission apparatuses 35 and 41. The communication line is not limited to the public line but may be any other communication line such as a local area network (LAN) or a wide area network (WAN).

According to the present embodiment, the magnetic card reader is used as the input means for inputting patient information. However, the input means for inputting patient information is not limited to the card reader but may be such a medium as an IC card or an optical card.

Furthermore, the system controller 30 may be provided with the capability of the remote controller 43.

The optical endoscope 21 is not limited to a type of endoscope for transmitting an optical image using a system of relay lenses. Alternatively, a type of endoscope adopting an image guide for transmitting an optical image through a fiber bundle will do. Moreover, the operator in the operating room and the supporter in the control room can communicate a voice signal, though it is not illustrated.

Figure 5:
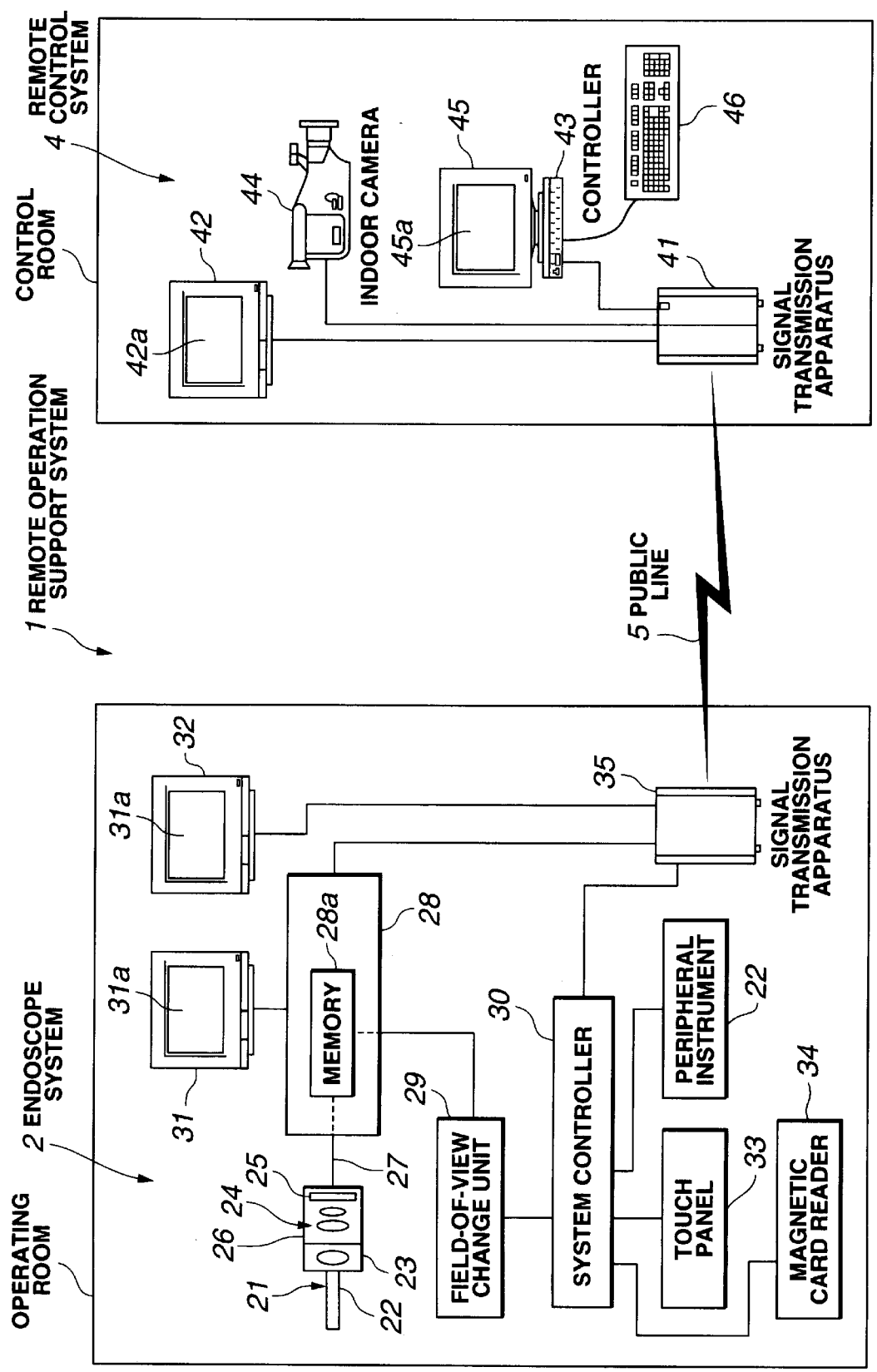
FIG. 5 is an explanatory diagram for explaining the method of controlling the field of view of an endoscopic camera in accordance with the second embodiment of the present invention.

FIG. 5 shows the overall configuration of a remote operation support system in accordance with the second embodiment of the present invention.

According to the first embodiment, when the supporter in the control room wants to change an image area or a viewing direction, at least one of the image formation optical system or CCD 25 in the TV camera 26 is moved using the field-of-view change unit 29. According to the present embodiment, in a remote operation support system 1A shown in FIG. 5, the field-of-view change unit 29 is used to control a read area of an image memory 28a included in the CCU 28 so as to thus change an image area or a viewing direction. The image memory 28a serves as an image accumulating means.

In other words, a read address of the image memory 28a is changed in order to change a viewing direction or the like. An endoscope employed is not limited to the aforesaid optical type but may be an electronic endoscope having an image formation optical system and a CCD incorporated in the distal part of an insertion unit. The other components and the operations and advantages are identical to those of the first embodiment. The same reference numerals will therefore be assigned to identical members. The description of the identical members will be omitted.

The present invention is not limited to the aforesaid embodiments. Different variants can be constructed without a departure from the gist of the invention.

Incidentally, in addition to the aforesaid embodiments, there are another embodiments according to which a remote operation support system permits an operator in an operating room to perform an operation with the help of a supporter in a remote place.

A medical-purpose endoscope system including an endoscope, which is disclosed in, for example, Japanese Unexamined Patent Publication No. 7-231896, has been proposed as a remote operation support system composed of a plurality of apparatuses. As for this sort of medical-purpose system, robotics surgery is attracting people's attention. Robotics surgery is such that a surgery robot connected to a system is controlled outside an operating room.

The idea of robotics surgery is to perform an operation by remotely controlling a surgery robot installed in an operating room. According to the robotics surgery, a site (hospital) where an experienced physician is not present is connected to a hospital at a remote site, in which an experienced physician is present, over a public line or the like. The hospitals are thus networked, whereby a patient can undergo as skilled an operation as an operation performed by an experienced physician.

Figure 12:
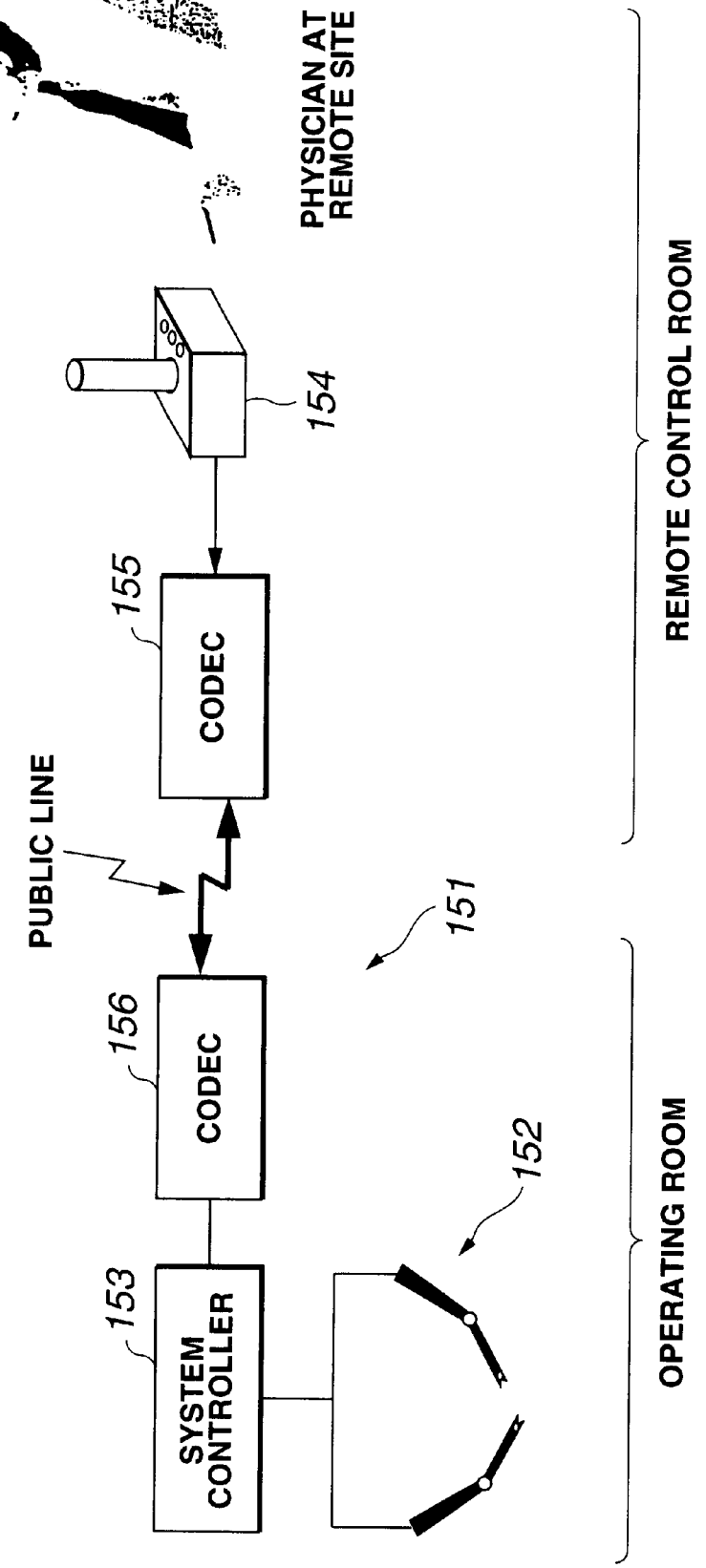
FIG. 12 shows the configuration in which conventional robotics surgery is implemented.

FIG. 12 shows one case where conventional robotics surgery is implemented. In FIG. 12, conventional robotics surgery 151 is such that a remotely controllable manipulator 152 installed in an operating room is controlled using a system controller 153. When a physician existent at a remote site moves a joystick 154 or any other remote control unit, the movement is converted into a signal, which can be transmitted over a public line using the integrated services digital network (ISDN), by a codec 155. A codec 156 installed in the operating room demodulates the signal and transmits it to the system controller 153. The system controller 153 further converts the signal received from the codec 156 so as to control the movement of the manipulator 152.

However, as far as the foregoing conventional robotics surgery is concerned, when a physician existent in an operating room and a physician existent at a remote site perform an operation in a team, the physician in the operating room cannot help judging the contents of manipulation, which is performed by the physician at the remote site, from the action of a manipulator or any other controlled apparatus. In the conventional robotics surgery, therefore, the physicians must mutually check the contents of manipulations performed by the mate in efforts to avoid such an incident that their surgical actions become inconsistent or their manipulations become contradictory. This poses a problem in that the physicians cannot proceed with teamwork efficiently in real-time.

According to another embodiment to be described later, there is provided a remote operation support system capable of inexpensively, accurately, and efficiently controlling the action of a controlled apparatus using a remote control unit by means of a voice signal. The controller apparatus is installed in an operating room, while the remote control unit is handled by a physician existent at a remote site. Moreover, the remote operation support system can convey the contents of manipulations performed by the physician existent at the remote site to the physician existent in the operating room by voice.

According to the present embodiment, there is provided a remote operation support system making it possible to check if the actions of a controlled apparatus installed in an operating room are controlled in conformity with manipulations performed by a physician existent at a remote site. Herein, a physical movement of a remote control unit handled by the physician existent at the remote site is conveyed to an operating room using a voice signal. Voice expressing the physical movement made by the physician at the remote site is conveyed to the operating room.

According to the present embodiment, there is provided a remote operation support system for controlling the actions of a controlled apparatus according to a manipulation signal output from a remote control unit. The remote operation support system consists of a remote control unit, a signal conversion unit, a voice generation unit, and a control unit. The remote control unit converts a physical movement into an electric signal and outputs the electric signal as a manipulation signal used to manipulate the controlled apparatus. The signal conversion unit converts the electric signal output from the remote control unit into a voice signal, which expresses a physical movement associated with the electric signal, according to a voice conversion table. The voice generation unit outputs a voice signal converted by the signal conversion unit as voice. The control unit controls the actions of the controlled apparatus according to the manipulation signal output from the remote control unit.

Moreover, a remote operation support system in accordance with the present embodiment has a remote control unit and a signal conversion unit installed at a remote site, and has a voice signal generation unit and a control unit installed in an operating room. The remote control unit converts a physical movement into an electric signal and outputs the electric signal as a manipulation signal. The signal conversion unit converts the electric signal produced by the remote control unit into a voice signal that expresses a physical movement associated with the electric signal. The voice signal generation unit outputs the voice signal as voice. The control unit controls the actions of the controlled apparatus according to the manipulation signal output from the remote control unit.

Figure 6:
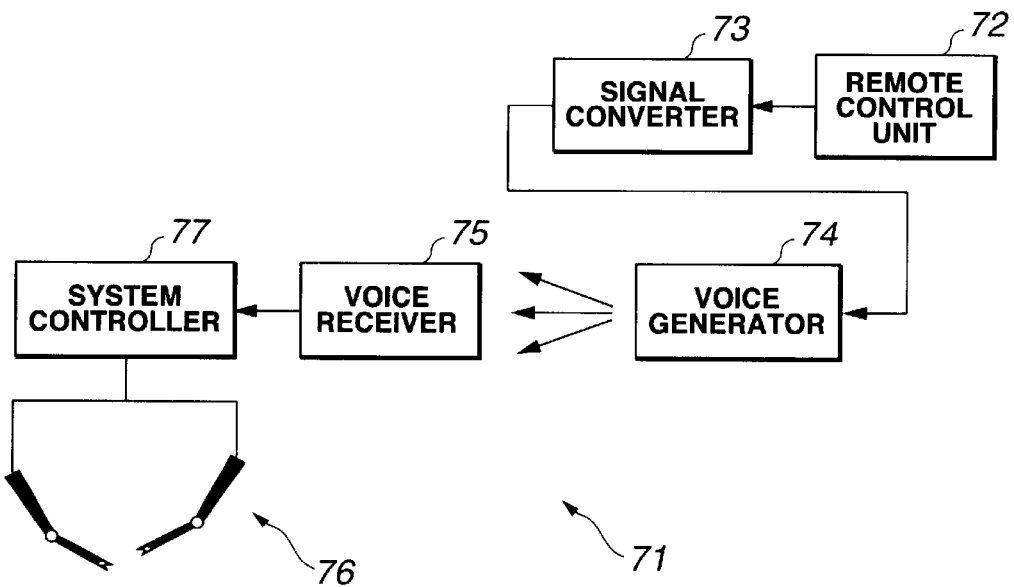
FIG. 6 to FIG. 8 relate to the third embodiment of the present invention.
Figure 7:
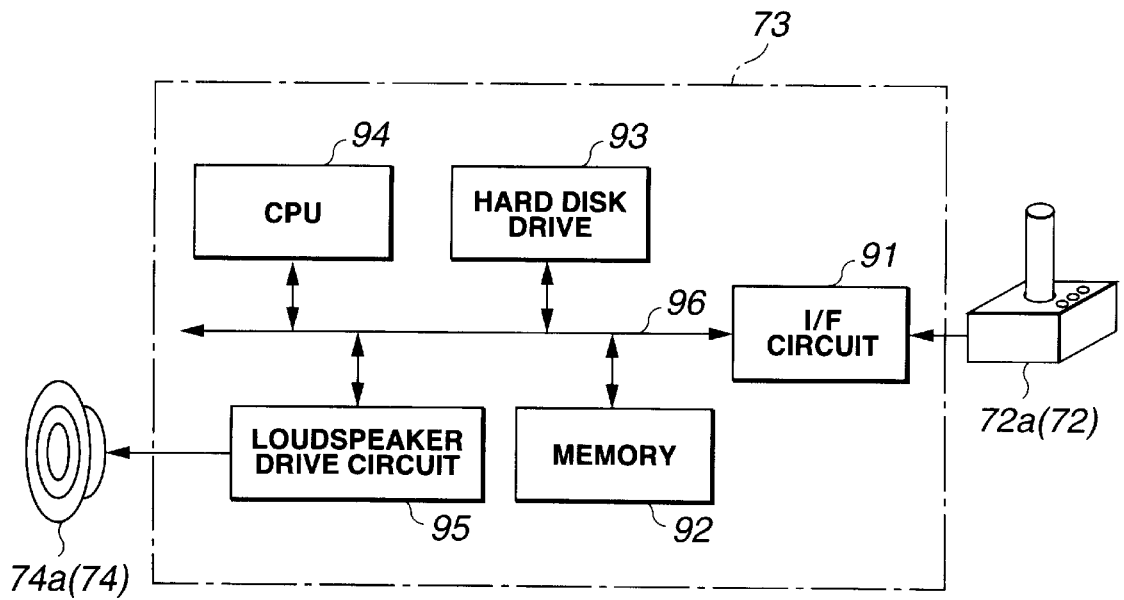
Figure 8:
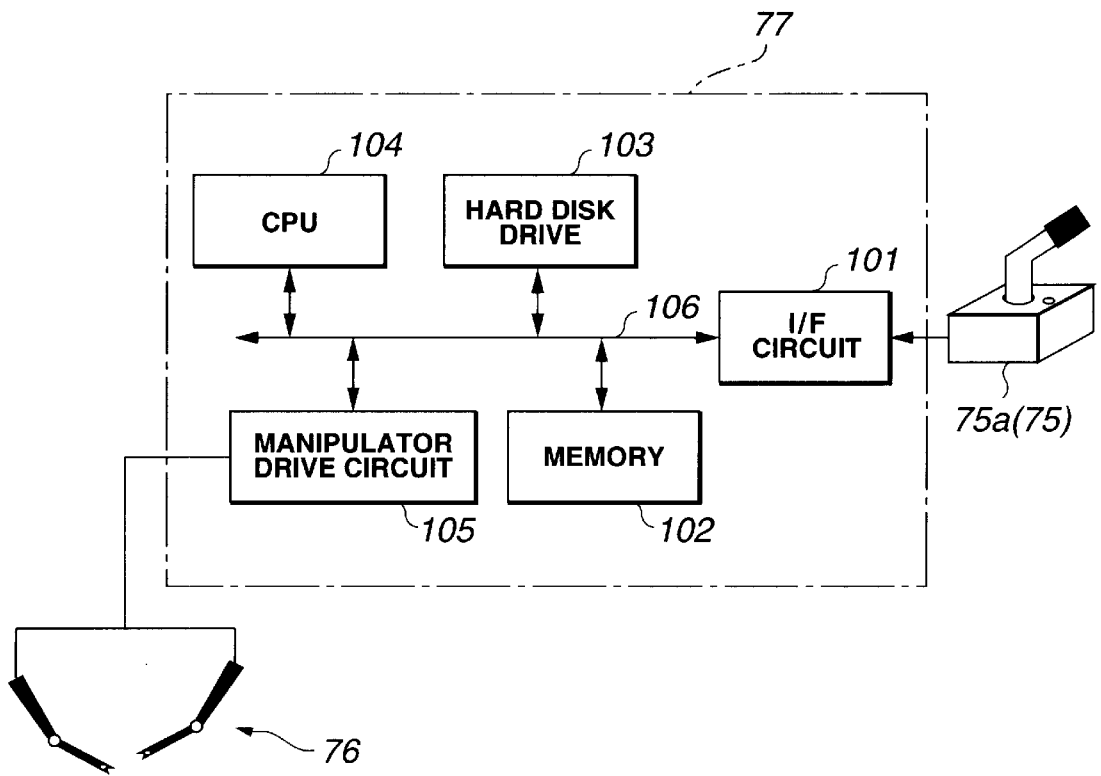

FIG. 6 to FIG. 8 relate to the third embodiment of the present invention. FIG. 6 shows the configuration of a remote operation support system. FIG. 7 shows the configuration of a signal converter shown in FIG. 3. FIG. 8 shows the configuration of a system controller shown in FIG. 6.

As shown in FIG. 6, a remote operation support system 71 in accordance with the present embodiment consists of a remote control unit 72, a signal converter 73, a voice generator 74, a voice receiver 75, and a system controller 77. The remote control unit 72 outputs an electric signal representing a physical movement (manipulation). The signal converter 73 converts the electric signal output from the remote control unit 72 into a voice transmission signal conformable to a predetermined protocol based on the electric signal output from the remote control unit 72. The voice transmission signal is a voice signal expressing a physical movement associated with the electric signal output from the remote control unit 72 that converts a physical movement into a signal and outputs the signal. The voice generator 74 generates predetermined voice according to the voice transmission signal sent from the signal converter 73. The voice receiver 75 receives voice generated by the voice generator 74. The system controller 77 drives and controls a manipulator 76 that is an example of a controlled apparatus having a high-frequency electric cautery, which is not shown, according to voice received by the voice receiver 75.

The remote control unit 72 and signal converter 73 are installed at a remote site, while the voice generator 74, voice receiver 75, manipulator 76, and system controller 77 are installed in an operating room. A transmission signal output from the signal converter 73 at the remote site is transmitted to the voice generator 74 in the operating room over a general public line.

The signal converter 73 consists of, as shown in FIG. 7, an interface circuit 91, a memory 92, a CPU 94, and a loudspeaker drive circuit 95 that are interconnected over an internal bus 96. The interface circuit 91 inputs a manipulation signal that expresses a physical movement of a remote control unit 72, for example, a joystick 72a and is produced by manipulating the remote control unit 72 back and forth or right and left. The interface circuit 91 then digitizes the manipulation signal and outputs numerical data. The numerical manipulation data output from the interface circuit 91 is stored in the memory 92. The CPU 94 collates the manipulation data stored in the memory 92 with a conversion table, which is shown in Table 1, stored in advance in a hard disk 93, and judges the movement of the joystick 72a. The conversion table is used to convert a physical movement into a voice signal expressing a physical movement associated with the electric signal output from the remote control unit 72 that converts a physical movement into a signal and outputs the signal. The loudspeaker drive circuit 95 outputs a transmission signal (analog voice signal), with which voice is generated by a loudspeaker 74a that serves as the voice generator 74, according to the result of judgment made by the CPU 94.

TABLE 1

| Code output from interface circuit 21 | Result of judgment made by CPU 24 | Sounding pattern |
| --- | --- | --- |
| 00100 | Leftward movement | Move it left. |
| 00101 | Rightward movement | Move it right. |
| 00110 | Forward movement | Move it forward. |
| 00111 | Backward movement | Move it backward. |
| 01000 | Advancement | Advance it. |
| 01001 | Withdrawal | Withdraw it. |
| 01010 | Catch | Catch it. |
| 01011 | Free | Free it. |
| 01110 | Cut | Apply high-frequency current. |

The joystick 72a has a switch that is not shown. The switch is used to selectively instruct a physical movement such as "Catch," "Free," or "Cut."

The system controller 77 consists of, as shown in FIG. 3, an interface circuit 101, a memory 102, a CPU 104, and a manipulator drive circuit 105 that are interconnected over an internal bus 106. The interface circuit 101 inputs a reception signal from a microphone 75a that serves as a voice reciever 75 and that receives voice generated by the loudspeaker 74a serving as the voice generator 74. The interface circuit 101 then digitizes the reception signal and output numerical data. The numerical voice data output from the interface circuit 101 is stored in the memory 102. The CPU 104 collates voice data stored in the memory 102 with a conversion table, which is shown in Table 2, stored in advance a hard disk 103, and judges control to be given to the manipulator 76. The manipulator drive circuit 105 drives and controls the manipulator 76 according to the results of judgement made by the CPU 104.

TABLE 2

| Code output from interface circuit 31 | Result of judgment made by CPU 34 | Control given to manipulator |
| --- | --- | --- |
| 00100 | Leftward movement | Move it left. |
| 00101 | Rightward movement | Move it right. |
| 00110 | Forward movement | Move it forward. |
| 00111 | Backward movement | Move it backward. |
| 01000 | Advancement | Advance it. |
| 01001 | Withdrawal | Withdraw it. |
| 01010 | Catch | Catch it. |
| 01011 | Free | Free it. |
| 01110 | Cut | Apply high-frequency current. |

Operations exerted by the present embodiment having the foregoing components will be described below.

When the joystick 72a serving as the remote control unit is moved (manipulated) physically or back and forth or right and left, if the switch that is not shown is manipulated, a manipulation signal is input to the interface circuit 91 in the signal converter 73. The interface circuit 91 digitizes the manipulation signal and stores numerical data in the memory 92.

The CPU 94 collates manipulation data stored in the memory 92 with the conversion table shown in Table 1 and stored in advance in the hard disk 93, and judges the movement of the joystick 72a. The CPU 94 controls the loudspeaker drive circuit 95 so that the loudspeaker drive circuit 95 will output a transmission signal, with which voice is generated by the loudspeaker 74a serving as the voice generator 74, according to the result of judgment. The transmission signal is an analog voice signal expressing a physical movement associated with the electric signal output from the remote control unit 72 that converts a physical movement into an electric signal and outputs the electric signal.

For example, when the joystick 72a is turned left, the interface circuit 91 generates manipulation data "00100." The manipulation data "00100" is stored in the memory 92. The CPU 94 references the conversion table, which is shown in Table 1, stored in advance in the hard disk 93. The CPU 94 then instructs the loudspeaker drive circuit 95 to output a transmission signal (analog voice signal) representing an associated message "Move it left."

On the other hand, voice is generated by the loudspeaker 74a serving as the voice generator 74 according to the transmission signal (analog voice signal) sent from the loudspeaker drive circuit 95. The voice is heard by an operator existent in the operating room, and received by the microphone 75a serving as the voice receiver 75. The interface circuit 101 in the system controller 77 digitizes the input reception signal and stores numerical data in the memory 102.

The CPU 104 collates voice data stored in the memory 102 with the conversion table, which is shown in Table 2, stored in advance in the hard disk 103, and judges control to be given to the manipulator 76. The CPU 104 controls the manipulator drive circuit 105 so as to drive and control the manipulator 76 according to the result of judgment.

For example, when an output of the interface circuit 101 is "01110," the CPU 104 activates a high-frequency electric cautery, which is not shown, connected to the manipulator 76 according to the conversion table in Table 2. Consequently, a lesion is cut with high-frequency current flowing from the distal end of the manipulator 76.

As mentioned above, according to the present embodiment, the physical movement (manipulation) of the joystick 72a serving as the remote control unit installed at a remote site is converted into a voice transmission signal (analog voice signal) according to the conversion table prepared in advance. The voice transmission signal is transmitted to an operating room over a general public line. The manipulation performed on the joystick 72a at the remote site is therefore inexpensively, accurately, and efficiently transmitted using a voice signal. Moreover, owing to voice uttered based on the voice signal, it can be checked if the manipulation performed at the remote site has been converted into a signal correctly. Furthermore, the contents of manipulation performed on the remote control unit at the remote site can be accurately conveyed to the operating room by voice.

Moreover, generally, in voice recognition, an identification rate at which an unspecified speaker can be identified is low. In the present embodiment, voice is converted into a unique voice signal. The identification rate can therefore be raised.

Furthermore, since an operator wears a mask in an operating room, the sound of verbal instructions uttered actually is so unclear that the identification rate deteriorates. According to the present embodiment, this will not take place.

Figure 9:
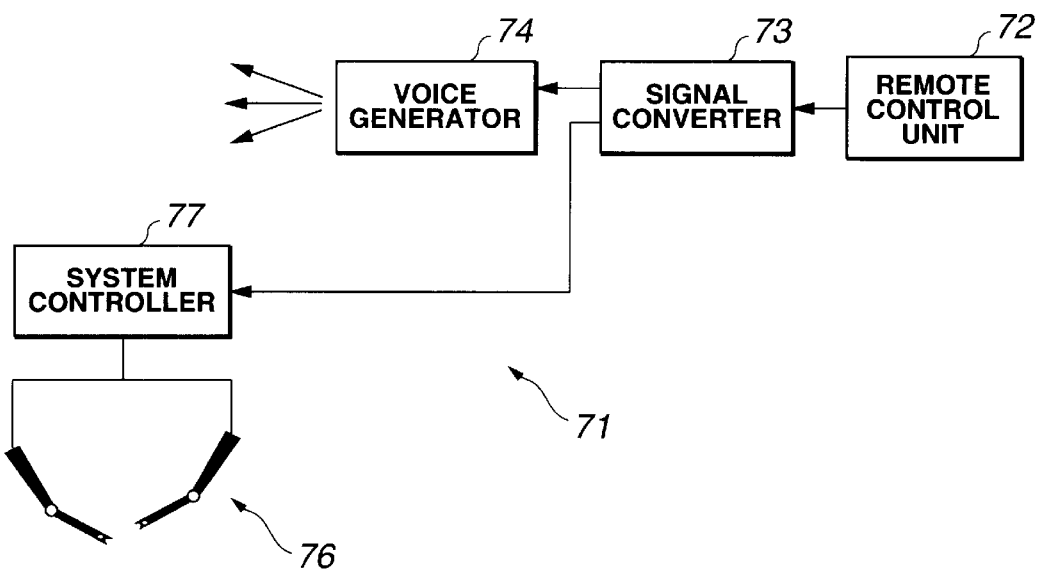
FIG. 9 shows the configuration of a remote operation support system in accordance with the fourth embodiment of the present invention.

FIG. 9 shows the configuration of a remote operation support system in accordance with the fourth embodiment of the present invention.

The second embodiment is nearly identical to the first embodiment. Different components alone will be described. The same reference numerals will be assigned to identical components and the description of the components will be omitted.

In the present embodiment, as shown in FIG. 9, the voice receiver 75 and a voice recognition facility included in the system controller 77 that are included in the first embodiment are not included. An output terminal of the interface circuit 91 in the signal converter 73 is directly connected in series with the interface circuit 101 in the system controller 77 over a general public line.

A transmission signal (analog voice signal) sent from the loudspeaker drive circuit 95 in the signal converter 73 is transmitted to the loudspeaker 74a serving as the voice generator 74 over a general public line. Voice is generated based on manipulation performed on the joystick 72a from the loudspeaker 74a serving as the voice generator 74. The other components are identical to those of the first embodiment.

In the present embodiment, a control signal is directly transmitted from the interface circuit 91 in the signal converter 73 to the interface circuit 101 in the system controller 77 over a general public line according to the serial data transmission method. The control signal is used to control the manipulator 76 according to manipulation performed on the joystick 72a serving as the remote control unit. Moreover, voice is generated based on the manipulation performed on the joystick 72a from the loudspeaker 74a serving as the voice generator 74. The other operations are identical to those of the first embodiment.

As mentioned above, the present embodiment provides the same advantages as the third embodiment. In addition, a control signal. used to control the manipulator 76 according to manipulation performed on the joystick 72a is transmitted directly over a general public line according to the serial data transmission method. The voice recognition facility can therefore be omitted. This results in a more inexpensive system.

Figure 10:
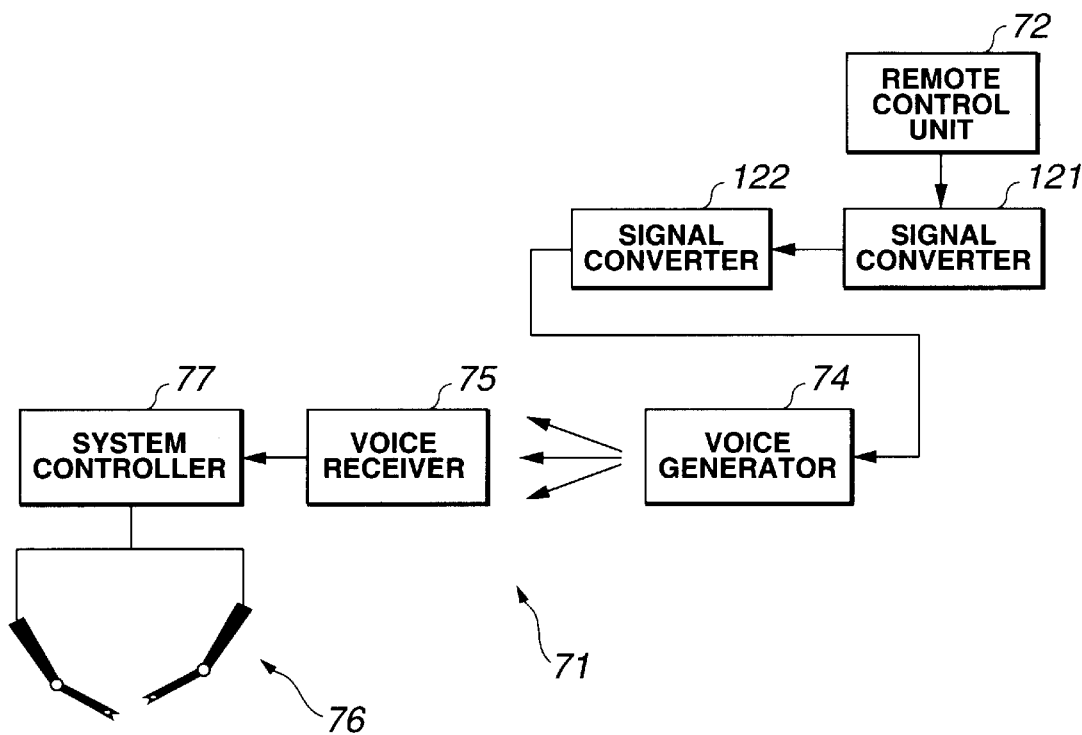
FIG. 10 shows the configuration of a remote operation support system in accordance with the fifth embodiment of the present invention.

FIG. 10 shows the configuration of a remote operation support system in accordance with the fifth embodiment of the present invention.

The fifth embodiment is nearly identical to the third embodiment. Different components alone will be described. The same reference numerals will be assigned to identical components and the description of the components will be omitted.

In the present embodiment, as shown in FIG. 10, a desktop conference system is composed of a signal converter 121 installed at a remote site and a signal converter 122 installed in an operating room. The signal converter 121 and signal converter 122 are designed to transfer images and voice in real-time via a sophisticated communication system conformable to a standard specified for the ISDN or LAN (standard H.320 for the ISDN or standard H.323 for the LAN). Television cameras and monitors, which are not shown, included in the signal converter 121 and signal converter 122 respectively are used to construct a desktop conference system using images and voice.

A voice signal is output from the signal converter 122 to the loudspeaker 74a serving as the voice generator 74 via the sophisticated communication system. The other components are identical to those of the first embodiment.

In the present embodiment, images and voice can be transferred in real-time via a sophisticated communication system. Television cameras and monitors, which are not shown, included in the signal converter 121 and signal converter 122 respectively are used to construct a desktop conference system using images and voice. The other operations are identical to those of the first embodiment.

As mentioned above, the present embodiment can provide the same advantages as the third embodiment. In addition, the manipulator 76 that is a. controlled apparatus can be controlled, and images and voice produced in both a remote site and operating room can be transferred in real-time. Consequently, an operation can be supported more meticulously.

Figure 11:
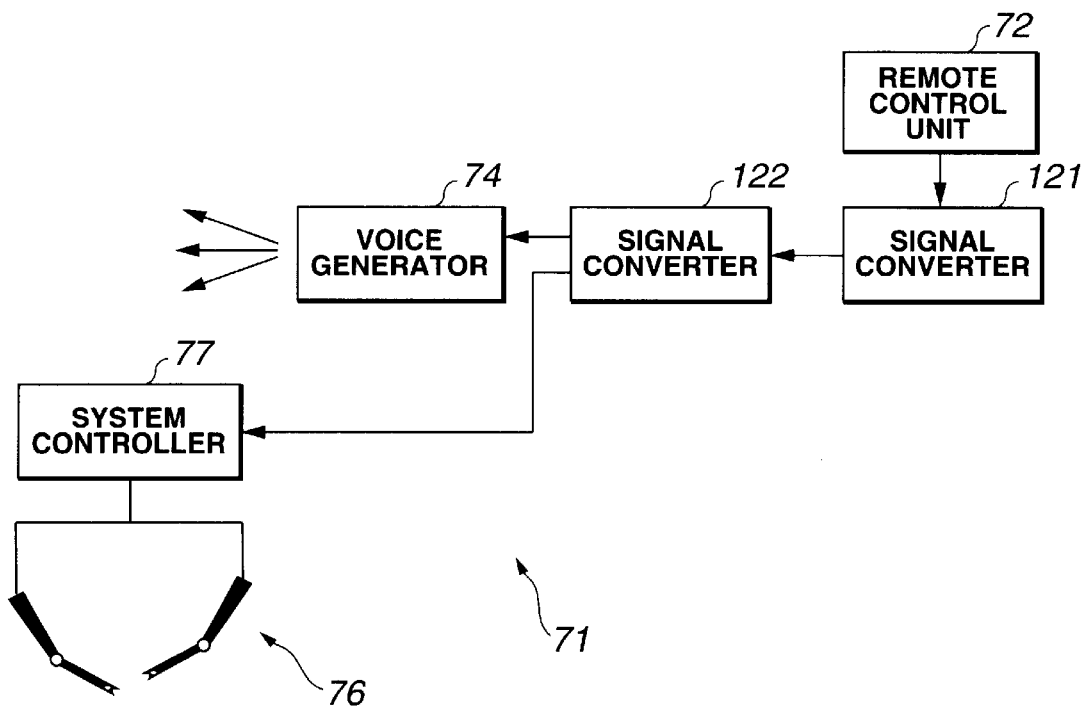
FIG. 11 shows the configuration of a remote operation support system in accordance with the sixth embodiment of the present invention.

FIG. 11 shows the configuration of a remote operation support system in accordance with the sixth embodiment of the present invention.

The sixth embodiment is nearly identical to the fifth embodiment. Different components alone will be described. The same reference numerals will be assigned to identical components and the description of the components will be omitted.

In the present embodiment, as shown in FIG. 11, the voice receiver 75 and the voice recognition facility included in the system controller 77 that are included in the third embodiment are not included. A control signal used to control the manipulator 76 according to manipulation performed on the joystick 72a and transmitted using a sophisticated communication system is sent from the signal converter 122 directly to the interface circuit 101 in the system controller 77 according to the serial data transmission method. A voice signal transmitted via the sophisticated communication system is transmitted to the loudspeaker 74a, which serves as the voice generator 74, from the signal converter 122. Voice is generated based on the manipulation performed on the joystick 72a from the loudspeaker 74a serving as the voice generator 74. The other components are identical to those of the fifth embodiment.

In the present embodiment, a control signal is transmitted from the signal converter 122 directly to the interface circuit 31 in the system controller 77 according to the serial data transmission method. The control signal is used to control the manipulator 76 according to manipulation performed on the joystick 72a and transmitted using a sophisticated communication system. Moreover, voice is generated based on the manipulation performed on the joystick 72a from the loudspeaker 74a serving as the voice generator 74. The other operations are identical to those of the fifth embodiment.

As mentioned above, the present embodiment can provide the same advantages as the fifth embodiment. In addition, a control signal used to control the manipulator 76 according to manipulation performed on the joystick 72a and transmitted using a sophisticated communication system is transmitted directly according to the serial data transmission method. The voice recognition facility can therefore be omitted. This results in a more inexpensive system than the system of the third embodiment.

In the aforesaid embodiments, the manipulator 76 is adopted as a controlled apparatus. The present invention is not limited to the manipulator. Alternatively, an endoscopic camera unit disclosed in, for example, Japanese Unexamined Patent Publication No. 7-231896, a light source apparatus, a high-frequency cautery, a pneumoperitoneum apparatus, or any other apparatus employed in an operation may be included as a controlled apparatus in a system. The aforesaid embodiments can still be adapted to such a system.

Moreover, the remote control means has been described by taking the joystick 72a for instance. The present invention is not limited to the joystick. Alternatively, the aforesaid embodiments can be adapted to a system including, for example, a pointing device such as a mouse or tablet or a keyboard as the remote control means.

In the present embodiment, it is apparent that a wide range of different embodiments can be constructed based on the invention without a departure from the spirit and scope of the invention. This invention will be limited by the appended claims but not restricted by any specific embodiment.

According to the aforesaid third to sixth embodiments, the constituent features described below are provided.

(1) A remote operation support system for controlling the actions of a controlled apparatus according to a manipulation signal output from a remote control unit, including:

a remote control unit for converting a physical movement into an electric signal and outputting the electric signal as a manipulation signal used to manipulate the controlled apparatus;

a signal conversion unit for converting the electric signal output from the remote control unit into a voice signal according to a voice conversion table;

a voice generation unit for outputting a voice signal converted by the signal conversion unit as voice; and a control unit for controlling the actions of the controlled apparatus according to the manipulation signal output from the remote control unit.

(2) A remote operation support system according to item (1), wherein the voice conversion table is used to convert an electric signal output from the remote control unit into a voice signal expressing a physical movement associated with the electric signal.

(3) A remote operation support system according to item (1), further including a voice reception unit for receiving voice output from the voice generation unit, wherein the control unit has a control signal conversion table used to generate a control signal, with which the controlled apparatus is driven and controlled, from a voice signal received by the voice reception unit.

(4) A remote operation support system according to item (1), wherein the control unit controls the actions of the controlled apparatus according to the voice signal based on the manipulation signal output from the remote control unit.

(5) A remote operation support system according to item (1), wherein the remote control unit and signal conversion unit are installed at a remote site, and the voice generation unit and control unit are installed in an operating room.

The third to sixth embodiments will be summarized below.

A remote operation support system consists mainly of a remote control unit, a signal converter, a voice generator, and a system controller. The remote control unit converts a physical movement into an electric signal and outputs the electric signal as a manipulation signal used to manipulate a controlled apparatus. The signal converter converts the electric signal output from the remote control unit into a voice signal, which expresses a physical movement associated with the electric signal, according to a voice conversion table. The voice generator utters predetermined voice according to a voice signal transmitted from the signal converter. The system controller controls the controlled apparatus such as a manipulator according to the manipulation signal output from the remote control unit. The remote control unit and signal converter are installed at a remote site, and the voice generator and system controller are installed in an operating room.

What is claimed is:

1. A remote operation support system in which an operating room and a control room located away from the operating room are linked using a communication line so that an operator present in the operating room can perform an operation while being supported by a supporter present in the control room, said remote operation support system comprising:

an endoscopic imaging system having an image formation optical system and an imaging device;

an image processing unit for converting an image signal produced by said endoscopic imaging system into a video signal;

a first display unit for displaying endoscopic images expressed by the video signal produced by said image processing unit;

a field-of-view change control unit for changing an image area or a viewing direction offered by said endoscopic imaging system; and a first signal transmission apparatus for transmitting a signal processed by said image processing unit over said communication line, and receiving an input signal over said communication line, wherein said endoscopic imaging system, image processing unit, first display unit, field-of-view change control unit, and first signal transmission apparatus are installed in the operating room, said remote operation support system further comprising:
a second signal transmission apparatus for receiving a signal from said first signal transmission apparatus over said transmission line, and transmitting a signal produced in the control room;
a second display unit for displaying an endoscopic video signal received by said second signal transmission apparatus; and
a control unit for producing an instruction signal used to change the image area or viewing direction represented by the endoscopic images displayed on said second display unit, and controlling said field-of-view change control unit in the operating room by way of said second signal transmission apparatus and communication line,
wherein said second signal transmission apparatus, second display unit, and control unit are installed in the control room.

2. A remote operation support system according to claim 1, wherein said field-of-view change control unit installed in said operating room changes the image area or viewing direction by changing the relative positions of said image formation optical system and imaging device included in said endoscopic imaging system.

3. A remote operation support system according to claim 1, wherein an instruction signal output from said control unit in the control room is produced by performing calculation based on a magnitude of shift observed on said second display unit.

4. A remote operation support system according to claim 1, wherein an instruction signal output from said control unit in the control room is produced by performing calculation based on a speed of shift observed on said second display unit.

5. A remote operation support system according to claim 1, wherein an instruction signal output from said control unit in the control room is produced by performing calculation based on an angle of shift observed on said second display unit.

6. A remote operation support method in which an operating room and a control room located away from the operating room are linked using a communication line so that an operator present in the operating room can perform an operation while being supported by a supporter present in the control room, said remote operation support method comprising the steps of:
imaging an intracavitary region of a certain object in the operating room;
processing an image signal expressing endoscopic images taken at said imaging step, and converting the image signal into a video signal;
transmitting the video signal to the control room;
receiving the video signal transmitted from the operating room;
displaying endoscopic images according to the received video signal;
producing and outputting an instruction signal used to change an image area or a viewing direction represented by the endoscopic images displayed at said displaying step;
transmitting the instruction signal produced and output at the preceding step to the operating room;
receiving the instruction signal transmitted at the preceding step in the operating room; and
changing the image area or viewing direction in the intracavitary region of the object according to the received instruction signal.

7. A remote operation support method according to claim 6, wherein said step of producing and outputting an instruction signal used to change an image area or a viewing direction represented by endoscopic images includes a designating step of designating a change point so that a field-of-view change instruction unit can change a field of view represented by the endoscopic images displayed on said display unit, and an arithmetic step of calculating the relationship between a destination point designated at said designating step and an origin.

8. A remote operation support method according to claim 7, wherein at said arithmetic step, a magnitude of shift is calculated based on two points designated on said display unit on which endoscopic images are displayed.

9. A remote operation support method according to claim 7, wherein at said arithmetic step, an angle of shift is calculated based on two points designated on said display unit on which endoscopic images are displayed.

10. A remote operation support method according to claim 7, wherein at said arithmetic step, a speed of shift is calculated based on two points designated on said display unit on which endoscopic images are displayed.

11. A remote operation support method according to claim 6, wherein at said step of producing and outputting an instruction signal used to change an image area or a viewing direction represented by endoscopic images, the relative positions of an image formation optical system and an imaging device included in said endoscopic imaging system are changed in order to change the image area or viewing direction.

12. A remote operation support method according to claim 6, wherein at said step of producing and outputting an instruction signal used to change an image area or a viewing direction represented by endoscopic images, a read area in an image accumulation unit included in said endoscopic imaging system is controlled in order to change the image area or an image position.

* * * * *